United States Patent
Lacey et al.

(10) Patent No.: US 7,065,173 B2
(45) Date of Patent: Jun. 20, 2006

(54) METHOD AND APPARATUS FOR THERMAL MANAGEMENT OF CT ELECTRONICS

(75) Inventors: Joseph J. Lacey, Cambridge, WI (US); Ashutosh Joshi, Waukesha, WI (US)

(73) Assignee: General Electric Company, Schenectady, NY (US)

( * ) Notice: Subject to any disclaimer, the term of this patent is extended or adjusted under 35 U.S.C. 154(b) by 115 days.

(21) Appl. No.: 10/725,756

(22) Filed: Dec. 2, 2003

(65) Prior Publication Data
US 2005/0117698 A1    Jun. 2, 2005

(51) Int. Cl.
*A61B 6/12* (2006.01)
(52) U.S. Cl. .................. 378/19; 250/370.15
(58) Field of Classification Search .............. 378/4, 378/19, 130, 199, 203, 210, 200, 98.8; 361/697, 361/696, 695, 694, 693, 691, 690, 688, 687; 250/370.15
See application file for complete search history.

(56) References Cited

U.S. PATENT DOCUMENTS

| | | | |
|---|---|---|---|
| 5,596,200 A * | 1/1997 | Sharma et al. | 250/370.14 |
| 6,411,672 B1 * | 6/2002 | Sasaki et al. | 378/19 |
| 6,668,910 B1 * | 12/2003 | Gawve | 165/80.3 |
| 2004/0195676 A1 * | 10/2004 | Quarre | 257/713 |

OTHER PUBLICATIONS

Chu et al. (1999); Application of thermoelectrics to cooling electronics:review and prospects; Eighteenth International Conference on Thermoelectrics; Aug. 29-Sep. 2, 1999; pp. 270-279.*

* cited by examiner

*Primary Examiner*—Courtney Thomas
(74) *Attorney, Agent, or Firm*—Joseph S. Heino; Patrick M. Bergin; Henry Policinski

(57) ABSTRACT

The present invention discloses a method and apparatus for cooling the electronics associated with Computed Tomography (CT) detector arrays. More particularly, the present invention discloses use of thermoelectric coolers in cooling CT detector electronics. The present invention also provides for using blowers or fans to recirculated air within a plenum for the cooling of CT detector electronics. The present invention also discloses the use of wick type heat pipes being placed either horizontally or with the evaporator end radially farther out than the condenser end such that rotational forces assist with heat flow through the heat pipe for cooling CT detector electronics. The present invention also discloses use of axial groove heat pipes to cool the CT detector electronics because they have enhanced performance under revolving conditions. Lastly, the present invention discloses use of heat sinks and circulation fans in combination with either type of heat pipe.

25 Claims, 7 Drawing Sheets

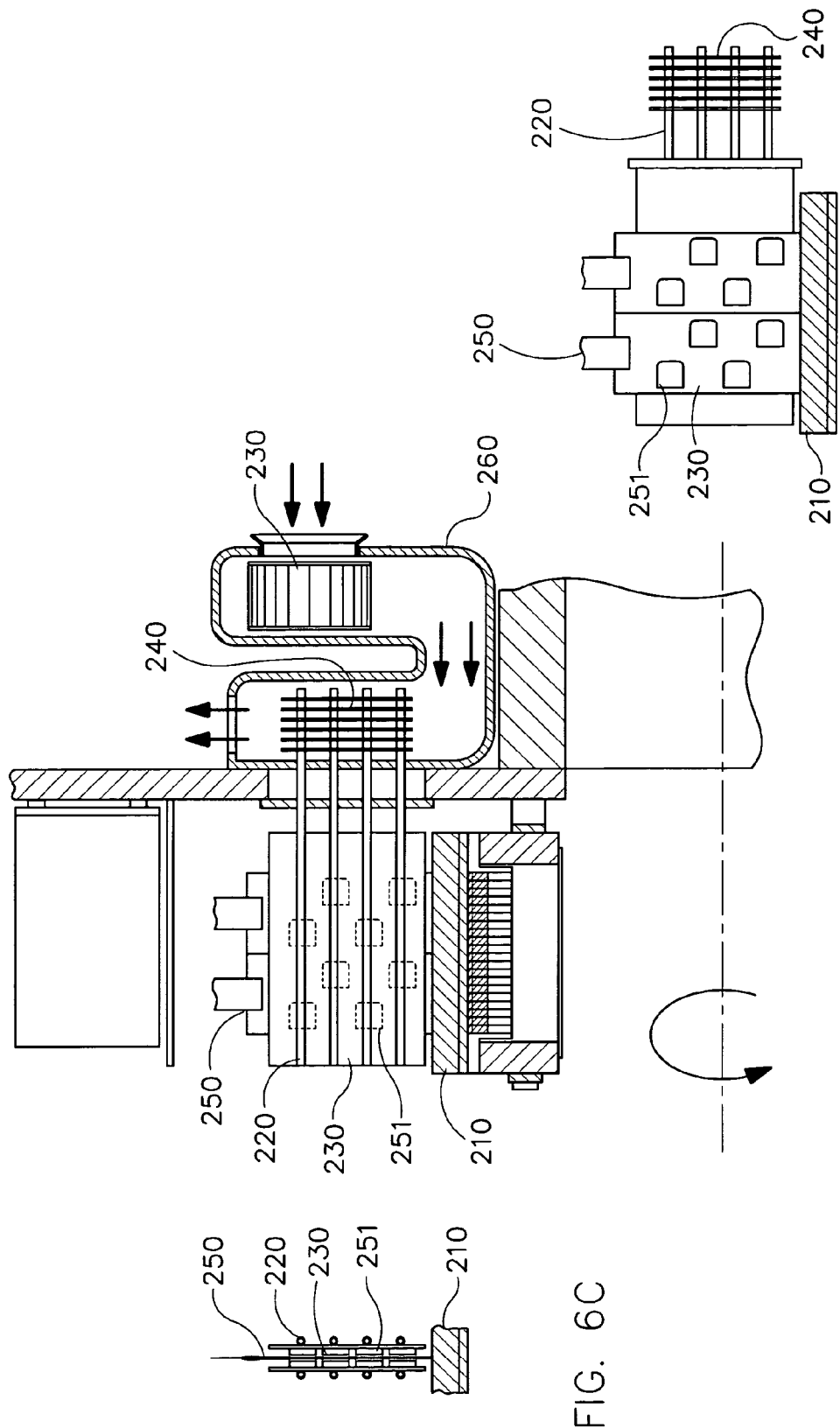

METHOD AND APPARATUS FOR THERMAL MANAGEMENT OF CT ELECTRONICS

BACKGROUND OF THE INVENTION

The present invention relates generally to computed tomography (CT) imaging systems. More particularly, it relates to a method and apparatus for cooling the electronics associated with CT scanners.

In at least some CT imaging system configurations, a stationary floor-mounted frame includes an x-ray source and a radiation detector array. The x-ray source projects a fan-shaped beam that is collimated to lie within an X-Y plane of a Cartesian coordinate system and is generally referred to as the "imaging plane". The x-ray beam passes through the object being imaged, such as a patient. The beam, after being attenuated by the object, impinges upon the array of radiation detectors. The intensity of the attenuated beam radiation received at the detector array is dependent upon the attenuation of the x-ray beam of the object. Each detector element of the array produces a separate electrical signal that is a measurement of the beam attenuation at the detector location. The attenuation measurements from all the detectors are acquired separately to produce a transmission profile. The x-ray source and the detector array are rotated with a gantry within the imaging plane and around the object to be imaged. The X-ray source typically includes an x-ray tube that emits an x-ray beam. The X-ray detectors typically include a collimator for collimating x-ray beams received at the detector. A scintillator is located adjacent the collimator and photodiodes are positioned adjacent the scintillator.

The power output by both the electronics associated with sensitive X-ray detectors and other components associated with CT imaging systems, including the x-ray tube itself, is increasing with each new generation of CT system. This increase in power output occurs while the packaging space remains constant or is decreasing. In particular, the electronics used in converting x-ray input to a useful electronic signal are rapidly becoming the dominant heat source within a CT system, rivaling the x-ray tube at steady state. Cooling of those electronics is made difficult for a number of reasons.

In order to accommodate higher signal densities and to reduce electronic noise, the electronics have been moved closer to the x-ray detector. Therefore, the high power electronics are conductively coupled to the highly temperature sensitive photodiode in the x-ray detector. Also, very little space is available between the analog to digital converters, which makes direct convective cooling difficult, if not impractical.

The photodiodes customarily employed in existing CT detectors only operate within a narrow range of temperatures. Therefore, any thermal control solution must not only prevent the heat from the electronics from reaching the photodiode but prevent the possibility of over cooling the photodiodes.

There are two factors that make direct convective cooling difficult in a CT detector gantry. The first is the fact that the air temperature within the gantry typically varies proportionally with the room ambient temperature. In general, the temperature of a room in which a CT imaging machine is used is specified and has a range of 11° C. Variation in cooling air temperature can lead to situations where the hot side heat is flowing to the photodiodes and may raise the temperature of the photodiodes above their set point temperature, which is, in general 36° C.±1° C. At the other extreme, the lowest cooling air temperature may cool the photodiode beyond its desired, or optimum operating temperature. The second factor hindering direct convective cooling is the fact that the electronics on a CT system rotate. This rotation tends to cause a decrease in airflow rate through any cooling fans that may be attached to the rotating side due to changes in the fan inlet flow boundary conditions. That is, because the inlet velocity vector tends towards being perpendicular to the flow direction, flow near the gantry covers produces lower pressure at the fan inlet. The rotation of the gantry also tends to cause mixing of the air inside the gantry thereby leading to a nearly instantaneous step change in the cooling air temperature. Another factor that needs to be considered in a direct convection cooling system is that, by virtue of allowing air to flow over the electronics, an opening has been created for the entrance of electronic fields. Thus, direct convection cooling has a negative impact on electromagnetic interference (EMI) shielding.

BRIEF SUMMARY OF THE INVENTION

The present invention provides for a localized rotating refrigeration system to actively control the air temperature of the cooling system. The invention further provides a system that is completely enclosed, thus reducing light exposure and particle contamination on the electronics. Air is recirculated within this enclosure using fans. The present invention also provides for ducting to direct the cooling air between the analog to digital converters and other components that produce heat in the detector array. The present invention also provides for the use of heat sinks on the analog to digital converters to maximize the amount of surface area for effective convective heat exchange.

Enclosing the CT detector electronics within the cooling system provides for precision temperature control which is virtually unaffected by gantry rotation. Complete enclosure of the system also means that EMI shielding is optimized and thus local shielding of the electronics can be reduced. The reduction in the local electronics shielding reduces the inherent conductive coupling between the electronics and the x-ray detector photo diode.

The advantage of the proposed invention is that it removes the problem of cooling air temperature fluctuation. Further, a lower cooling air temperature can be achieved than by simply using room air increasing the capability to remove power from the electronics. Another advantage of such a system is that the complete enclosure of electronics provides insulation against electromagnetic interference (EMI). That is, the system would be nearly immune to changes in internal air flow due to rotation and would provide the best possible EMI shielding.

Yet a further advantage of the present invention is that use of thermoelectric coolers (TECs) removes the siting problems associated with placing an air to liquid type refrigeration system on the stationary side. Complete enclosure of the system means that EMI shielding is optimized and thus local shielding of the electronics can be reduced. The reduction in the local electronics shielding reduces the inherent conductive coupling between the electronics and the x-ray detector photo diode.

The present invention provides for using a heat exchanger to remove heat from the recirculated air. One embodiment of the present invention provides for using a combination of a heat sink and a thermoelectric cooler to remove heat from the recirculated air. This embodiment of the invention also provides for controller and a feedback control mechanism which is primarily responsible for determining the temperature of the recirculating air and regulating the thermoelectric cooler to keep the cooling air within a specified temperature range.

The present invention further provides effective electronics cooling while minimizing the temperature conductive coupling between the x-ray detector and the electronics. In one embodiment, the present invention provides for an array of heat pipes coupled to a spreader plate that is thermally linked to the heat generating chips. Heat is then piped away from the electronics and removed using forced convection. In yet another embodiment, the present invention provides for placement of heat pipes within the circuit boards. Yet another embodiment of the present invention provides for the use of heat pipes between the electronics packages.

The present invention further provides for use of wick type heat pipes being placed either horizontally or with the evaporator end radially further out than the condenser end such that rotational forces assist with heat flow through the heat pipe. In general, under rotating loads, a wick style heat pipe will function properly as long as the radial capillary pumping forces within the heat pipe are not exceeded by the rotational forces.

In situations where the rotational forces are exceeded by the capillary pumping forces, other heat conduction methods can be used. For example, the present invention provides for use of a combination of a wick type heat pipe and an axial groove thermal siphon, or wickless heat pipe. Axial groove heat pipes have enhanced performance under revolving conditions. This is mainly due to the axial groove functioning as an Archimedes screw under rotating conditions.

The present invention also provides for an axial groove heat pipe wherein the heat pipe is oriented such that the evaporator end is either parallel to or lower than the condenser end. Therefore, the liquid in the condenser end is not required to flow against gravity to cool the electronics when the gantry is tilted.

The foregoing and other features of the present invention will be apparent from the detailed description that follows.

BRIEF DESCRIPTION OF THE DRAWINGS

FIG. 6C a schematic elevational view of A/D converters, spreader plate and heat pipes.

FIG. 6D is a schematic elevational view of yet another embodiment of the present invention.

FIG. 6E is a schematic elevational view of yet another embodiment of the present invention.

DETAILED DESCRIPTION OF THE INVENTION

Figure 1:
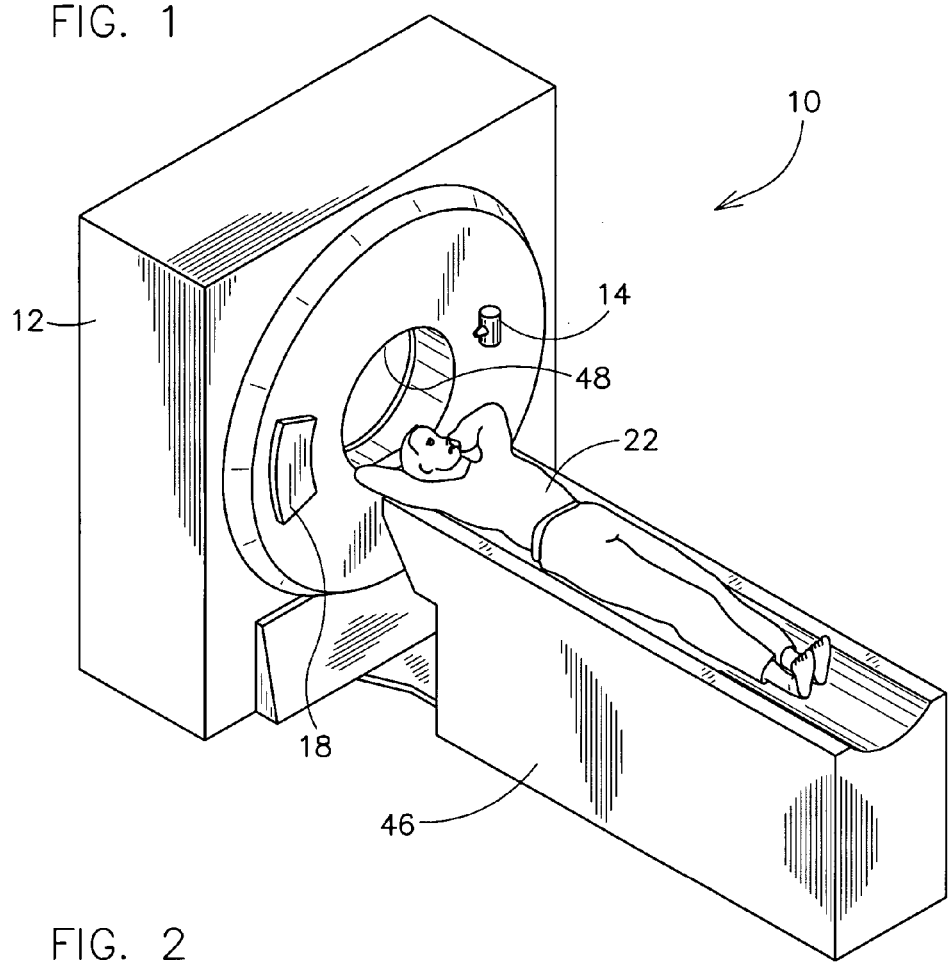
FIG. 1 is a pictorial view of a CT imaging system.
Figure 2:
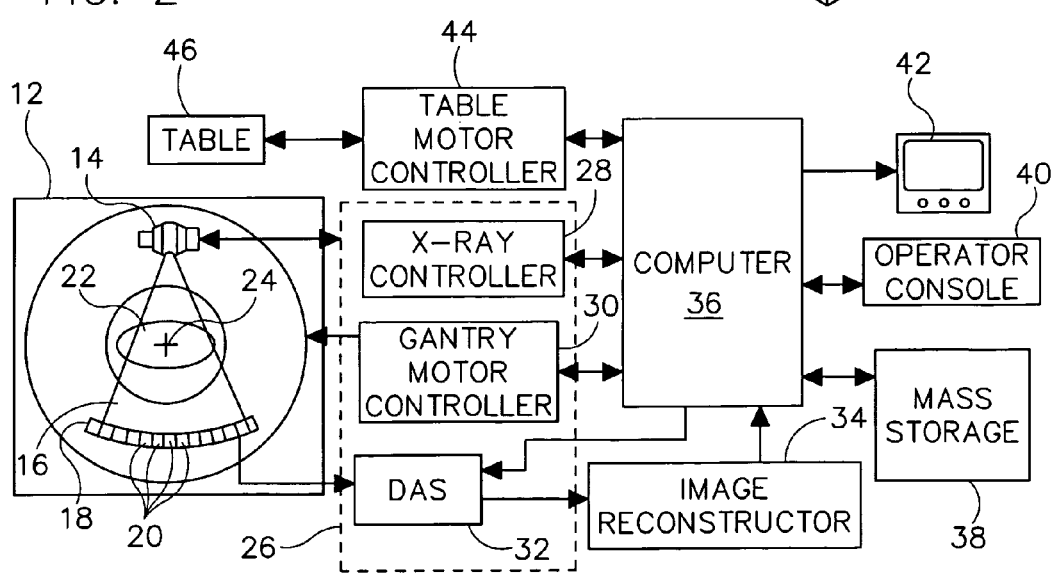
FIG. 2 is a block schematic of the system illustrated in FIG. 1.

Referring now to the drawings in detail wherein like-numbered elements correspond to like elements throughout, FIGS. 1 and 2 show a multi-slice scanning computed tomography (CT) imaging system 10. The CT imaging system 10 is shown as including a gantry 12 representative of a "third generation" CT imaging system. Gantry 12 has an X-ray source 14 that projects a beam of X-rays 16 toward a detector array 18 on the opposite side of gantry 12. Detector array 18 is formed by a plurality of detector rows (not shown) including a plurality of detector elements 20 which together sense the projected X-rays that pass through an object, such as a medical patient 22. Each detector element 20 produces an electrical signal that represents the intensity of an impinging X-ray beam and hence the attenuation of the beam as it passes through object or patient 22. During a scan to acquire X-ray projection data, gantry 12 and the components mounted thereon rotate about a center of rotation 24. FIG. 2 shows only a single row of detector elements 20 (i.e., a detector row). However, multislice detector array 18 includes a plurality of parallel detector rows of detector elements 20 so that projection data corresponding to a plurality of quasi-parallel or parallel slices can be acquired simultaneously during a scan.

Rotation of gantry 12 and the operation of X-ray source 14 are governed by a control mechanism 26 of CT system 10. Control mechanism 26 includes an X-ray controller 28 that provides power and timing signals to X-ray source 14 and a gantry motor controller 30 that controls the rotational speed and position of gantry 12. A data acquisition system (DAS) 32 in control mechanism 26 samples analog data received from detector elements 20 through a flex cable (not shown in FIGS. 1 and 2), and converts the data to digital signals for subsequent processing. An image reconstructor 34 receives sampled and digitized X-ray data from DAS 32 and performs high-speed image reconstruction. The reconstructed image is applied as an input to a computer 36 which stores the image in a mass storage device 38.

Computer 36 also receives commands and scanning parameters from an operator via console 40 that includes at least one input device such as a keyboard or a mouse. An associated cathode ray tube display 42 allows the operator to observe the reconstructed image and other data from computer 36. The operator supplied commands and parameters are used by computer 36 to provide control signals and information to DAS 32, X-ray controller 28 and gantry motor controller 30. In addition, computer 36 operates a table motor controller 44 which controls a motorized table 46 to position patient 22 in gantry 12. Particularly, table 46 moves portions of patient 22 through the gantry opening 48.

In one embodiment, computer 36 includes a device, for example, a floppy disk drive or CD-ROM drive, for reading instructions and/or data from a computer-readable medium, such as a floppy disk or CD-ROM. In another embodiment, computer 36 executes instructions stored in firmware (not shown). Computer 36 is programmed to perform functions described herein, accordingly, as used herein, the term "computer" is not limited to just those integrated circuits typically referred to in the art as computers, but more broadly refers to computers, processors, microcontrollers, microcomputers, programmable logic controllers, application specific integrated circuits, and other programmable circuits.

Figure 3:
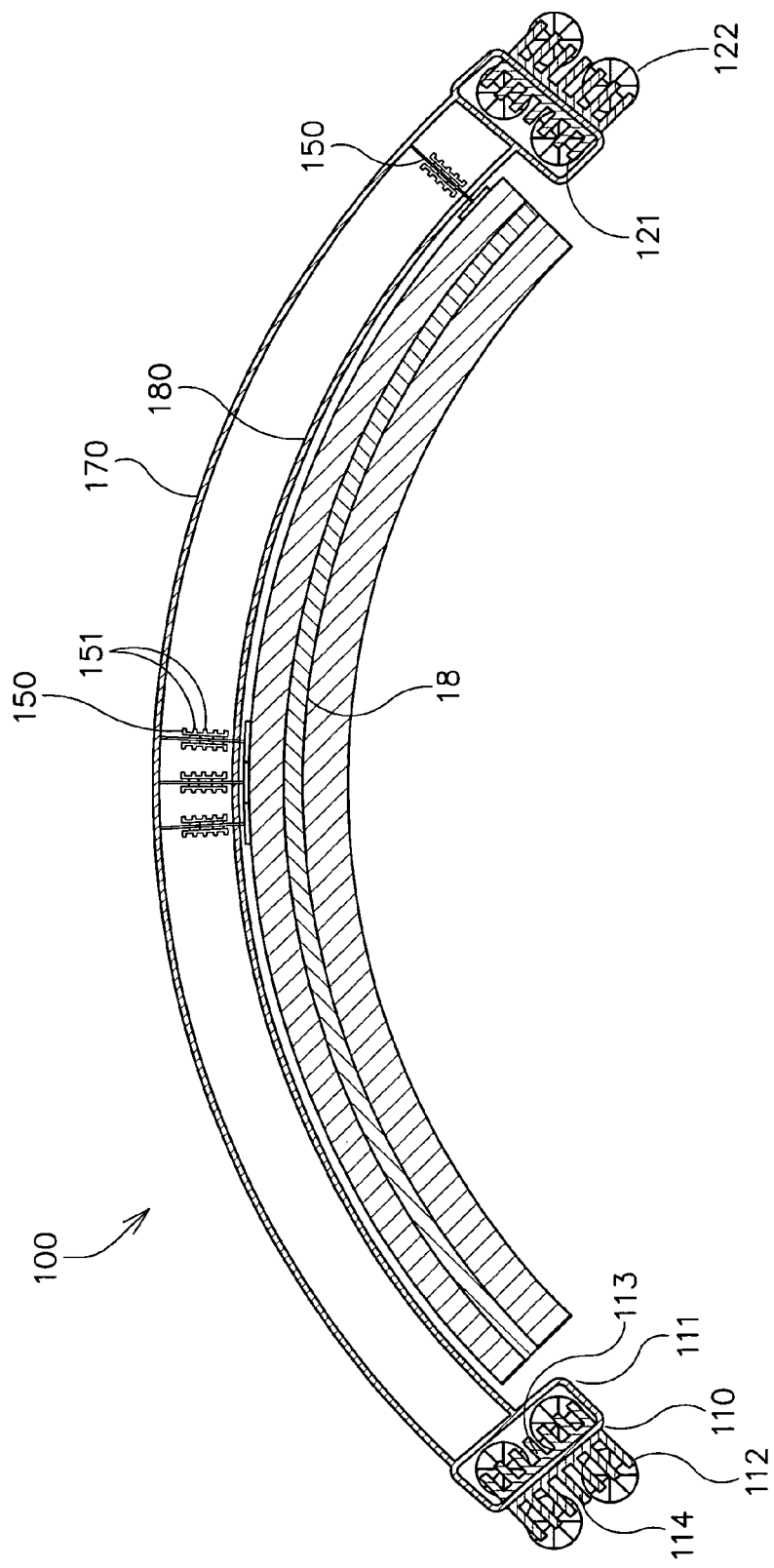
FIG. 3 is a front cross-sectional schematic view of the detector array of the present invention having an electronics cooling system.
Figure 4:
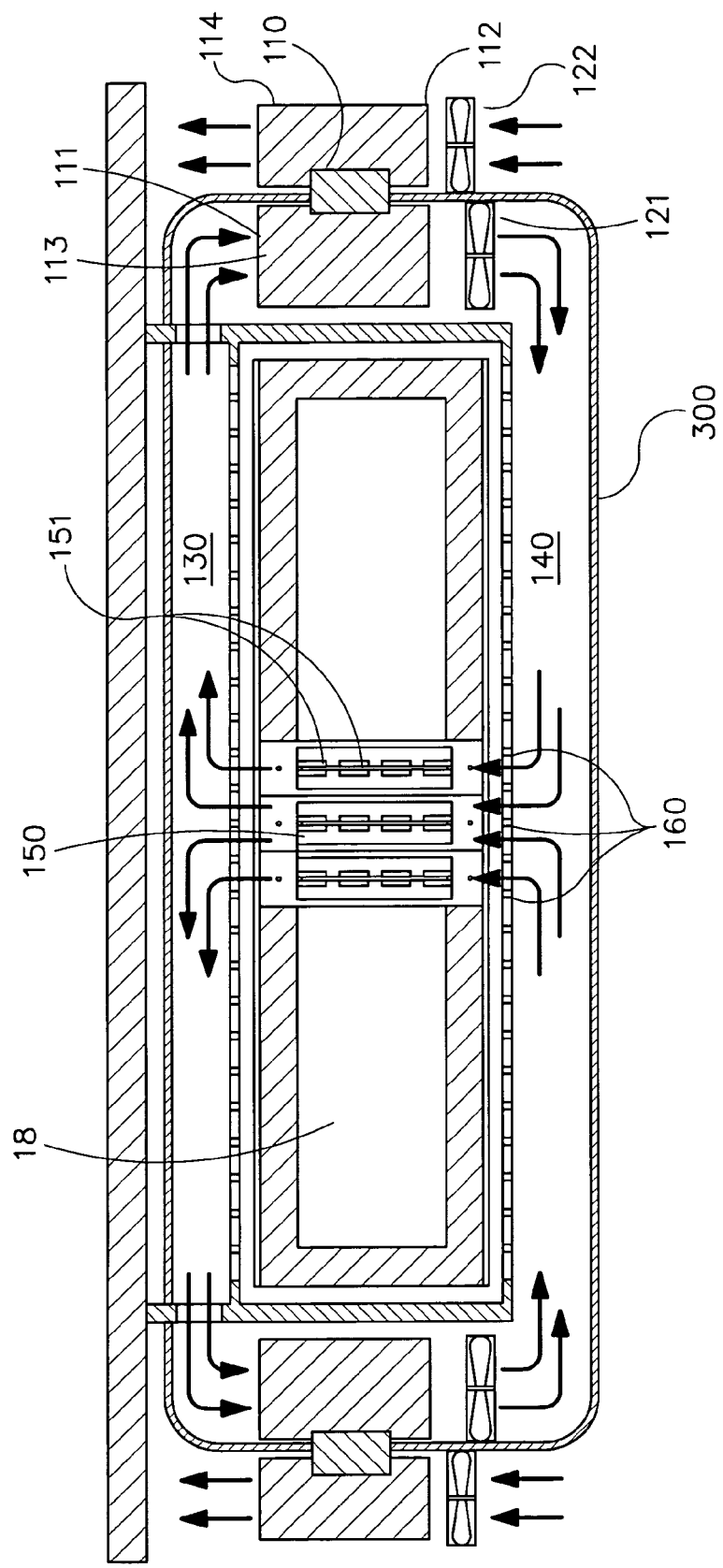
FIG. 4 is a top cross-sectional view of the electronics cooling system of FIG. 3 showing the configuration of the cooling system in more detail.

As discussed in the foregoing and shown in FIGS. 3 and 4, the present invention provides for a temperature regulation device for the electronics package employed in an image reconstruction process.

As shown in FIGS. 3 and 4, and in summary, the present invention makes use of a localized rotating refrigeration system 100 to actively control the air temperature of the cooling system. The system is completely enclosed by hot air plenum 130 and a cold air plenum 140 and recirculates the air via a fan or fans 121 through the cold air plenum and air past the hot analog to digital converters 150 and any other hot components to remove heat from the electronics. The air is then routed past a heat exchanger section consisting of the cold side of a thermoelectric cooler (TEC) 111. The hot side of the TEC 112 is located outside the enclosure consisting of the hot side plenum 130 and the cold side plenum 120 and pumps the heat from the hot side of the TEC 112 to the air outside the detector enclosure 300. One embodiment may also provide for regulating the TECs 110 by use of a controller in communication with a feedback control mechanism such that the cooling air temperature is regulated to a small temperature range of a few degrees Celsius by either increasing or decreasing fan speed.

More specifically, the present invention provides for a detector enclosure 300 generally comprising a cold air plenum 140 and a hot air plenum 130 to enclose the detector array 18 and the electronics associated therewith. Even more specifically, on one side of the detector array 18, the present invention provides for a cold air plenum 140. The cold air plenum 140 can be divided into two chambers such that cold air can be directed inwardly from both ends of the detector array 18. In this way, cold air can be distributed more evenly among the electronics 150 for more effective cooling. Obviously, the present invention could also provide for TECs 110 cooling multiple chambers within the detector enclosure 300. In fact, because of high heat loads produced by present electronics 150, several TECs 110, each employing fans 121 circulating cooled air through a cold air plenum 140, then through an electronics array 150, to a hot air plenum 130 and back to the cold side of a TEC 111 for cooling, may be required to cool the detector array electronics 150.

The cold air plenums are used to direct the cold air around the A/D converters 151 and the other electronics 150 that generate heat in the detector array. The present invention also provides for the use of baffles, or flow directors 160 to direct the air onto the electronics 150 more efficiently. In particular, the A/D converters 151 produce a significant amount of heat. However, the A/D converters are 151, in general, elongated and narrower than the photodiodes they represent. Therefore, air can be circulated between the A/D converters 151 for more specific cooling. The warmed air is then collected by the hot side plenum 130. The hot side plenum 130 directs the hot air to the cold side of the TEC 111, in the embodiment shown, at the end of the detector array 18.

At the end of the detector array 18 is the cold side of the TEC 111. The cold side of the TEC is also called the heat source, 113. Thermoelectric coolers 110, as are known in the art, are solid state heat pumps. Thermoelectric coolers are based on the Peltier Effect. In general, TEC units 111 serve to transfer heat from one planar unit to the other, in a manner and magnitude consistent with the electrical current flow through it. In general, TECs 110 function on the opposite principal to that of thermocouples. In other words, while a thermocouple operates on the principle that heat across two dissimilar metals produces a current, TECs 110 operate on the principle that current applied across two dissimilar materials causes a temperature differential.

The hot side of the TEC 112 is located outside the both the hot air plenum 130 and the cold air plenum 140, and in general, outside the detector enclosure 300. The TEC 110, in general, pumps heat to the cold side of the TEC 112 which features a heat sink 114. The heat sink 114 is then appropriately sized to dissipate the heat to the room 310. The heat sink 114 could simply rely on surface area and natural convection to dissipate heat, or as shown in FIGS. 3 and 4, employ forced convection with a fan 122 to blow outside air across the area of the heat sink 114. Further, the heat sink 114 need not be anything other than a surface of the hot side of the TEC 112. In one embodiment, the hot side of the TEC 112 may have fins, to aid in heat dissipation.

The detector enclosure 300 provided by the combination of the cold air plenum 140 and the hot air plenum 130 is also useful to prevent excess light from reaching the sensitive photodiodes as well as preventing dirt and dust from getting into the photodiodes and sensitive electronics. The cold air plenum 140 is also removable for service access to the electronics 150 and the detector array 18.

In FIG. 3, the detector array 18 shows a specific embodiment of the present invention. The detector array 18 is the curved inside section and is generally comprised of a plurality of detector elements. The detector elements are heated for optimal operation.

Specifically, the detector rail 18 is separated from the temperature control apparatus by an air flow barrier, or direct convection break 180. The air flow barrier 180 is designed to insulate the detector elements, which are required to be kept within a certain temperature range from the electronics 150, which need to be cooled below the temperature of the detector elements.

Next, shown in cross section, are the electronics 150, such as the analog to digital converters 151. As shown, each A/D converter 151 has a heat sink 152. The heat sinks 152 are designed to dissipate the heat produced by the A/D converters 151 as well as other electronics to the air flowing through the electronics 150. For purposes of illustration, and as shown in FIG. 3, the air would be either flowing straight up out of the page or straight down into the page. The air is then contained around the electronics 150 by the digital plug bulkhead 170, which seals the electronics 150 from light, dust and other impurities that could damage the electronics 150.

FIG. 4 shows the actual airflow pattern employed with one embodiment of the present invention. Specifically, the temperature control device of the present invention is comprised of a cold air plenum 140, a hot air plenum 130, a thermoelectric cooler 110, heat sink and a plurality of circulation fans 121, 122. In this embodiment, the detector rail is divided into two zones which are each cooled by a thermoelectric cooler 110. This reduces the possibility of large temperature gradients across the electronics 150. While only two zones are shown, more could be used to provide better temperature regulation.

FIG. 4 also shows the forced convection from the cold side of the TEC 110, through the cold side plenum 140, where it is directed through the electronics 150, picks up heat from the heat sinks attached to the electronics and is directed, or drawn to the hot side plenum 130. The hot side plenum 130 then directs air to the cold side of the TEC 111, which refrigerates the air on the cold side of the TEC 111.

The hot side of the TEC 112, or heat sink, which is outside of the CT imaging machine, is also cooled using an outside cooling fan 122.

In summary, the present invention provides for a method and apparatus for cooling the electronics of a CT detector array 18, said detector array comprised of a plurality of photodiodes, said photodiodes being connected to electronics 150 including analog to digital converters 151, said analog to digital converters 151 generating heat when in operation: a hot side plenum 130 for accumulating air heated by the electronics 150; a thermoelectric cooler 110 attached to one end of the hot side plenum 130; a heat source 113 connected in thermal relationship to the thermal electric cooler 111; a cold side plenum 140 for directing air across the electronics 150; and a circulation fan 121 to draw air from the hot side plenum 130 across the thermoelectric cooler 110 and into the cold side plenum 140. In particular embodiments, the electronics temperature regulating apparatus further comprises a temperature measurement device in electronic communication with the temperature measurement device such that the programmable temperature controller regulates the temperature of electronics by either increasing circulation fan 121 speed or increasing power to the thermoelectric cooler 110.

In yet another embodiment of the present invention, electronics cooling is accomplished using heat pipes 220. The present invention provides a CT imaging machine having the x-ray tube 14 and detector array 18 with the detector array 18 having an electronics package 250. One of the primary components of the electronics package, and one of the largest contributors to problematic heating, is the analog to digital converter 251. This second embodiment of the present invention provides for a plurality of heat pipes 220 to regulate the temperature of the electronics package 251.

A heat pipe 220, as is well known in the art, is a kind of heat transfer device which transports the latent heat of a working fluid charged within a closed tube from phase transformation. The working fluid undergoes phase transformation within the heat pipe 220 and circulates between the evaporation side and the condensation side. Evaporated vapor moves from the evaporation side to the condensation side by pressure gradient, while the condensate returns to the condensation side by the capillary force of the wick, the gravitational force or the centrifugal force within the heat pipe 220.

Heat pipes 220 having no wick and, in general, relying on gravitational and/or centrifugal forces are called thermal siphons. In general, wick type heat pipes operate well regardless of the positions of the evaporation side and the condensation side, but the evaporation side should be placed at higher position than the condensation side for the thermal siphon.

Figure 5B:
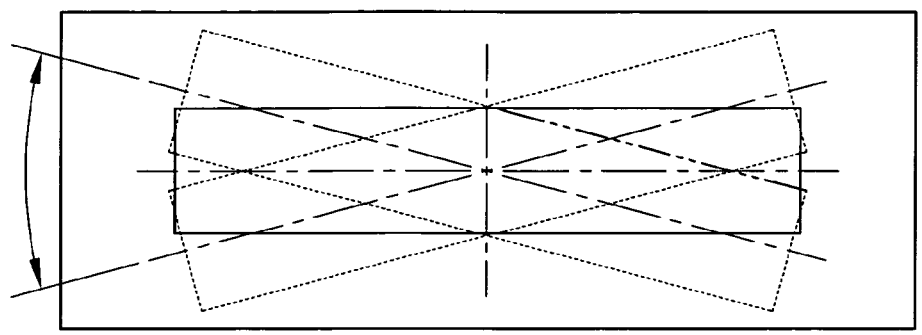
FIG. 5B is a schematic of a CT imaging system in profile showing the gantry's maximum degree of tilt.
Figure 5A:
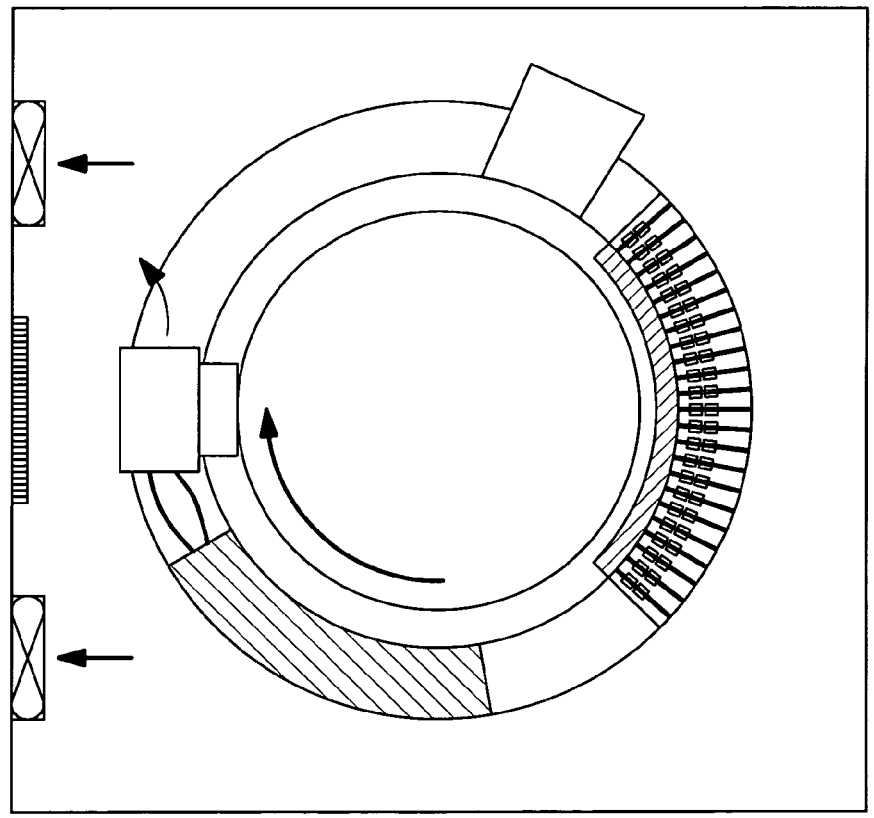
FIG. 5A is a schematic of a CT imaging system showing the detector array and analog to digital electronics.

As shown in FIG. 5, the CT imaging system includes an x-ray tube 14, a detector assembly 18, and an electronics package 250, generally comprised of a plurality of analog to digital converters 251. The A/D converters 251 produce a substantial amount of heat when the imaging system is in operation.

Figure 6B:
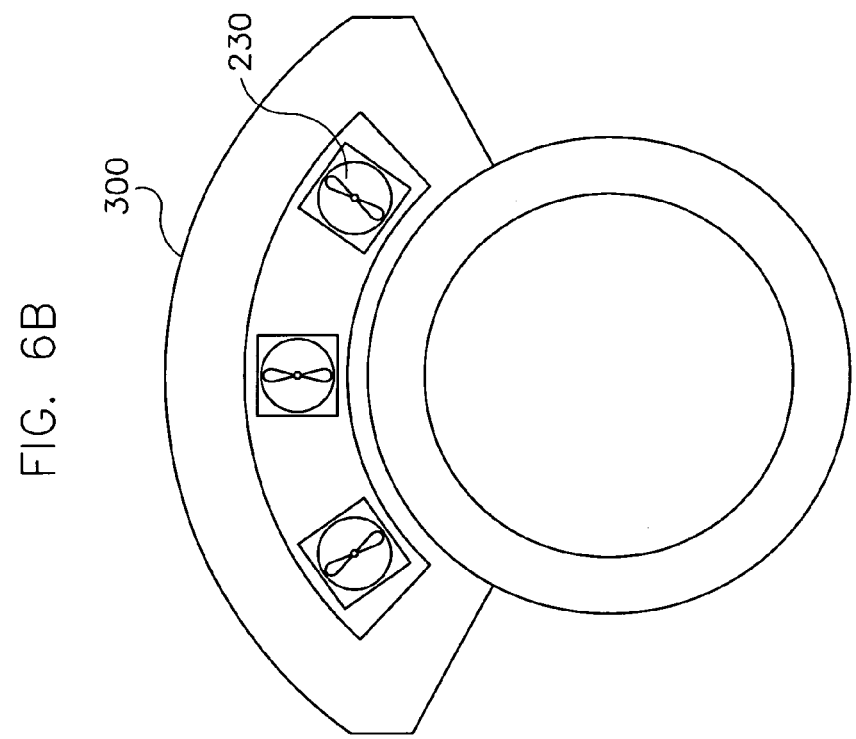
FIG. 6B is a schematic elevational view of end of the gantry of a CT imaging machine.
Figure 6A:
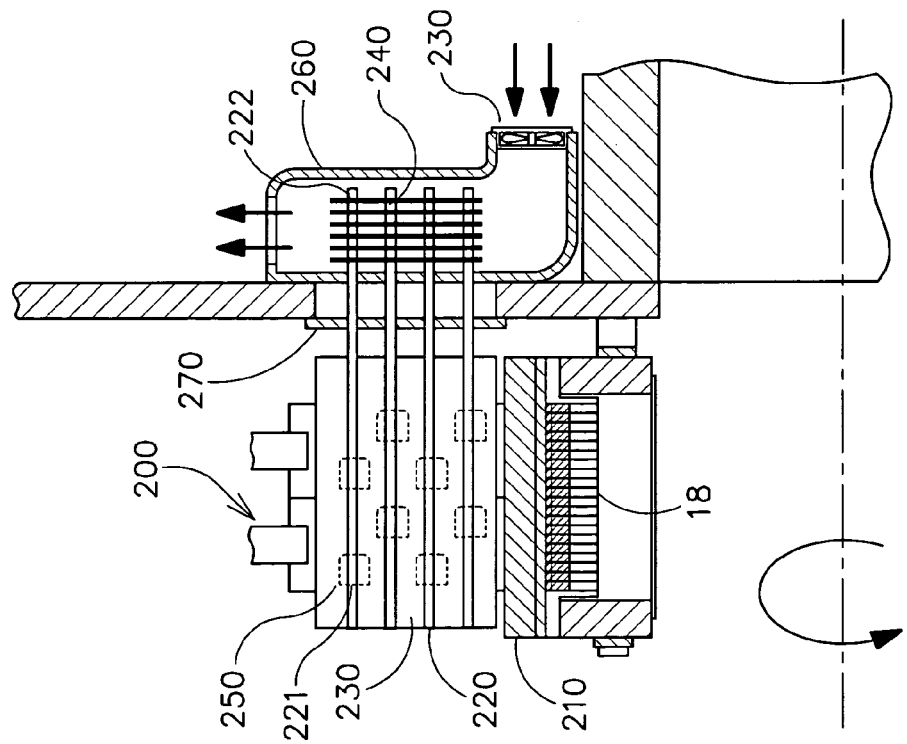
FIG. 6A is a schematic view of a detector array and the associated electronics showing one embodiment of the present invention.

Therefore, as shown in FIG. 6A, the present invention has provided a spreader plate 200 having plurality of heat pipes 210 running generally horizontally across the spreader plate 200. FIG. 6A is perhaps best viewed in contrast to FIG. 6B, which shows an end view of the CT detector gantry 12. The spreader plates 200 enable a more even heat distribution to reach the heat pipes 220. Under rotating conditions the wick style heat pipes 220 work most effectively when they are as horizontal as possible or with the evaporator end farther from the center of rotation such that the rotational forces assist with the heat flow.

Figure 8A:
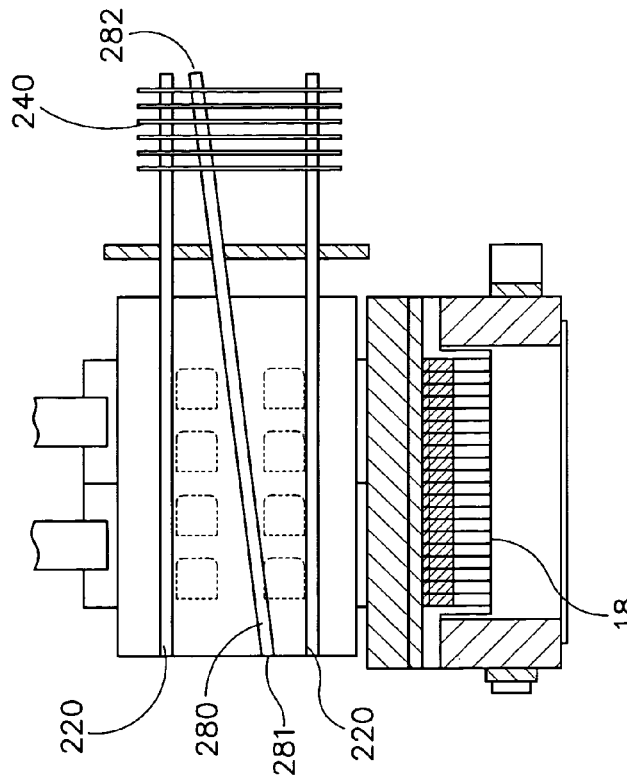
FIG. 8A is a schematic view of an axial groove thermal siphon employed with a wick style heat pipe.
Figure 8B:
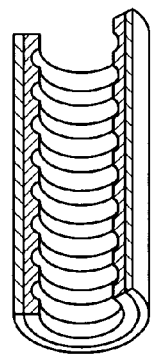
FIG. 8B is a schematic view of an axial groove thermal siphon.
Figure 7A:
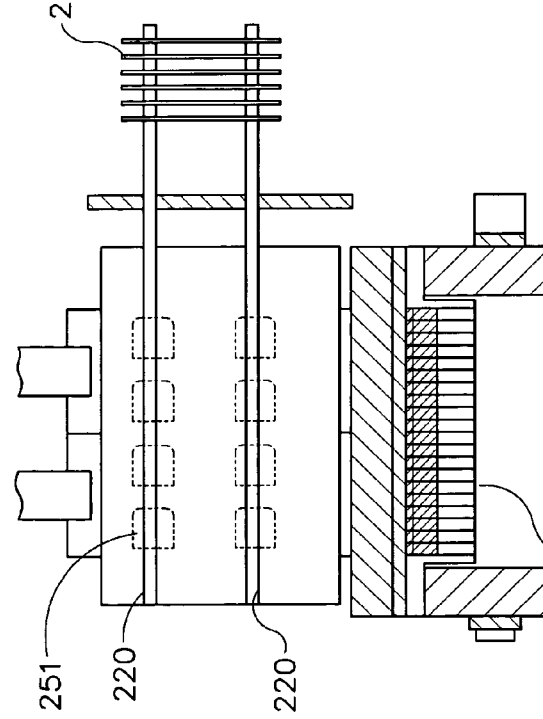
FIG. 7A is a schematic view of yet another embodiment of the present invention.
Figure 7B:
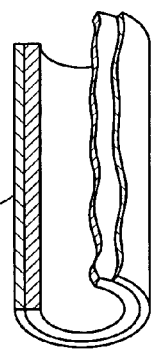
FIG. 7B is a schematic view of a wick style heat pipe.

In yet another embodiment as shown in FIGS. 8A and 8B, especially important when rotational loading is too large for a wick type heat pipe to function effectively, the present invention provides for use of a wickless heat pipe, or axial groove thermal siphon 280 in combination with heat pipes 220. The performance of a thermal siphon 280 is actually enhanced under rotating conditions. The use of thermal siphons 280 in combination with wick style heat pipes ensures that the electronics will remain cool under both stationary and rotating conditions, the thermal siphons 280 functioning optimally under rotating conditions and the heat pipes under stationary conditions.

Obviously, there are many ways of attaching heat pipes and thermal siphons, however, a few are depicted in FIGS. 6A, 6C, 6D and 6E. In general, both types of heat pipes 220, 280 may either be embedded into the spreader plate 230 as shown in FIG. 6E or external to the spreader plate 230 as shown in FIGS. 6C and 6D. However, in regards to the axial groove heat pipes 280, and as shown in FIG. 8A, in order to be effective, the axial groove thermal siphon 280 should be placed at an angle such that the evaporator end 281 is lower than the condenser end 282. This ensures that the liquid in the condenser end 282 will not have to flow against gravity.

As before, the detector array 18 and sensitive electronics package 250 are enclosed within a sealed plenum, although no forced convection occurs inside the plenum. Instead, the heat pipes 220 are used to direct heat from the electronics package 250 to the outside room air. The heat pipes 220 then continue outside the CT and terminate in a heat sink 240. The heat sink 220 is enclosed within a blower cage or plenum 260 and is cooled by a circulation fan 230.

In yet another embodiment, as shown in FIG. 6E, the present invention employs a spreader plate 230 having a plurality of embedded heat pipes 220. The heat pipes 220 terminate in a heat sink 240. The heat sink 240 is cooled by a centrifugal blower 230 inside a plenum 260. Obviously, unless the heat sink 240 is very large, forced convection across the heat sink 240 is required to keep the heat sink 240 at a reasonable temperature. However, whether a circulation fan 230 or a centrifugal blower is used is irrelevant.

Frequently, a layer of insulation 210 is positioned between the detector array 18 and the electronics package 250. Also, frequently, a sealing surface 270 is required around the heat pipes 220 where they exit the plenum to the heat sink 240.

The foregoing description has been presented for purposes of illustration. It is to be understood that widely different embodiments of the invention may be constructed without departing from the spirit and the scope of the present invention. It should also be understood that the present invention is not limited to the specific embodiments described in the specification, except as defined in the appended claims.

What is claimed is:

1. An apparatus for regulating the temperature of Computed Tomography (CT) detector array electronics for computed tomography imaging machines comprising;

a hot air plenum for accumulating air from the electronics;

a thermoelectric cooler connected at one end to the hot side plenum;

a heat sink connected to the thermoelectric cooler;

a cold air plenum for directing cool air to the electronics; and a circulation fan to draw air from the hot side plenum across the thermoelectric cooler and into the cold side plenum.

2. The electronics temperature regulating apparatus of claim 1 further comprising a temperature measurement device.

3. The electronics temperature regulating apparatus of claim 2 further comprising a programmable temperature controller, said temperature controller in electronic communication with the temperature measurement device.

4. The electronics temperature regulating apparatus of claim 3 wherein said programmable temperature controller regulates the temperature of electronics by either increasing circulation fan speed or increasing power to the thermoelectric cooler.

5. The electronics temperature regulating apparatus of claim 3 wherein heat sinks are attached to some or all of the heat generating electronics.

6. A method for regulating the temperature of CT detector array electronics for CT imaging machines wherein the CT detector electronics primarily consist of analog to digital converters that are separated from each other and permit the passage of air, comprising the steps of:
blowing air through the electronics;
collecting the air;
cooling the air with a thermoelectric cooler.

7. The method for cooling the electronics of a CT detector array of claim 6 further comprising the step of providing a hot air plenum for collecting the air.

8. The method for cooling the electronics of a CT detector array of claim 7 further comprising the step of providing a circulation fan to circulate cool air through the electronics.

9. The method for cooling the electronics of a CT detector array of claim 8 further comprising the step of regulating the temperature of the cooling air by increasing or decreasing the speed of the circulation fan.

10. A method for regulating the temperature of Computed Tomography (CT) detector array electronics for CT imaging machines wherein there are apertures between the CT detector electronics, comprising the steps of:
sealing the CT electronics in an enclosure;
circulating air through the enclosure; and
using a thermoelectric cooler to cool the circulating air.

11. An apparatus for cooling the electronics of a CT detector array, said detector array comprised of a plurality of photodiodes, said photodiodes being connected to analog to digital converters, said analog to digital converters generating heat when in operation:
a hot side plenum for accumulating air heated by the electronics;
a thermoelectric cooler attached to one end of the hot side plenum;
a heat sink connected in thermal relationship to the thermal electric cooler;
a cold side plenum for directing air across the electronics; and
a circulation fan to draw air from the hot side plenum across the thermoelectric cooler and into the cold side plenum.

12. The electronics temperature regulating apparatus of claim 11 further comprising a temperature measurement device.

13. The electronics temperature regulating apparatus of claim 12 further comprising a programmable temperature controller, said temperature controller in electronic communication with the temperature measurement device.

14. The electronics temperature regulating apparatus of claim 13 wherein said programmable temperature controller regulates the temperature of electronics by either increasing circulation fan speed or increasing power to the thermoelectric cooler.

15. An apparatus for regulating the temperature of CT detector array electronics for computed tomography imaging machines comprising:
a plurality of heat pipes in thermal contact with the electronics, said heat pipes extending outwardly from a spreader plate;
a heat sink attached to said heat pipes;
a blower cage containing said spreader plate; and
a circulation fan for blowing air across the heat sink.

16. The electronics temperature regulating apparatus of claim 15 further comprising a spreader plate interposed between the electronics and the heat pipes, said spreader plate providing an efficient thermal contact surface between the electronics and the heat pipe.

17. The electronics temperature regulating apparatus of claim 16 further comprising an axial groove siphon, said axial groove siphon being in thermal contact with the electronics.

18. The electronics temperature regulating apparatus of claim 17 wherein said axial groove siphon is situated at an angle such that the evaporator end is lower than the condenser end.

19. The electronics temperature regulating apparatus of claim 15 further comprising a temperature measurement device within the blower cage.

20. The electronics temperature regulating apparatus of claim 19 further comprising a programmable temperature controller, said temperature controller in electronic communication with the temperature measurement device.

21. The electronics temperature regulating apparatus of claim 20 wherein said programmable temperature controller regulates the temperature of electronics by either increasing circulation fan speed.

22. The electronics temperature regulating apparatus of claim 19 further comprising a temperature measurement device within the blower cage.

23. The electronics temperature regulating apparatus of claim 20 further comprising a programmable temperature controller, said temperature controller in electronic communication with the temperature measurement device.

24. The electronics temperature regulating apparatus of claim 21 wherein said programmable temperature controller regulates the temperature of electronics by either increasing circulation fan speed.

25. An apparatus for regulating the temperature of CT detector array electronics for computed tomography imaging machines comprising:
a spreader plate in thermal contact with the electronics;
a plurality of heat pipes, attached to the spreader plate, said heat pipes being in thermal contact with the spreader plate;
a heat sink attached to said spreader heat pipes;
a blower cage containing said spreader plate; and
a circulation fan for blowing air across the heat sink.

* * * * *